United States Patent [19]

Mirell

[11] Patent Number: 4,690,130

[45] Date of Patent: Sep. 1, 1987

[54] ELECTROMAGNETIC THERAPY CONTROL SYSTEM

[76] Inventor: Stuart G. Mirell, 10816 Cushdon Ave., Los Angeles, Calif. 90064

[21] Appl. No.: 811,159

[22] Filed: Dec. 19, 1985

[51] Int. Cl.[4] ............................................. A61B 17/52
[52] U.S. Cl. .................................................. 128/1.3
[58] Field of Search .................................. 128/1.1–1.3, 128/1 R, 654; 252/62.53, 62.54; 424/1.1, 85

[56] References Cited

U.S. PATENT DOCUMENTS

| | | | |
|---|---|---|---|
| 3,474,777 | 10/1969 | Figg et al. | 128/1.1 |
| 4,096,862 | 6/1978 | DeLuca | 128/1.2 |
| 4,106,488 | 8/1978 | Gordon | 128/1.1 |
| 4,247,406 | 1/1981 | Widder et al. | 252/62.54 |
| 4,269,826 | 5/1981 | Zimmermann | 128/1.1 |
| 4,303,636 | 12/1981 | Gordon | 128/1.1 |
| 4,331,654 | 5/1982 | Morris | 252/62.53 |
| 4,348,376 | 9/1982 | Goldenberg | 128/1.1 |
| 4,454,234 | 6/1984 | Czerlinksi | 427/127 |
| 4,460,559 | 7/1984 | Goldenberg | 424/1.1 |
| 4,590,922 | 5/1986 | Gordon | 128/1.1 |

FOREIGN PATENT DOCUMENTS 2508802 1/1983 France ........................... 128/1.3

Primary Examiner—Kyle L. Howell
Assistant Examiner—Max F. Hindenberg
Attorney, Agent, or Firm—Poms, Smith, Lande & Rose

[57] ABSTRACT

Chemotherapy may be selectively localized to a tumor located at a point well within the human body by physically associating the chemotherapy agent with magnetic material having a Curie point temperature slightly above the normal temperature of the human body. Both materials may be associated with protein microspheres such as human serum albumin. By applying a magnetic field to the tumor location and then applying electromagnetic radiation to heat the Curie point magnetic material (so that it loses its magnetic properties), away from the tumor site, but not at the tumor site, the unheated magnetic material and the physically associated chemotherapy agent will be localized at the tumor. Radioactive material may also be employed to facilitate imaging of the concentration of the microspheres and for radiation treatment.

13 Claims, 9 Drawing Figures

ELECTROMAGNETIC THERAPY CONTROL SYSTEM

FIELD OF THE INVENTION

This invention relates to the control of Curie Point material for medical and other purposes by magnetic and high frequency electrical fields.

BACKGROUND OF THE INVENTION

It has previously been proposed to localize the application of chemotherapy agents for the treatment of cancer tumors by the physical association of magnetic materials and chemotherapy agents in protein microspheres, such as human serum albumin, or other microscopic carriers. In this regard, reference is made to Medical World News, Aug. 21, 1978, p. 57; "Magnetic Targeting of Microspheres in Blood Flow", by C. F. Driscoll et al., Microvascular Research 27, 353–369 (1984), and "Experimental Methods in Cancer Therapeutics", by Kenneth J. Widder et al, Jl. of Pharm. Sciences, Vol. 71, No. 4, Apr. 1982 pp. 379–386. Related patents include K. J. Widder U.S. Pat. No. 4,247,406; R. T. Gordon U.S. Pat. No. 4,106,488; G. H. Czerlinski U.S. Pat. No. 4,454,234. The Widder patent relates to the process mentioned above. The Gordon patent relates to the heating of particles which may be magnetic, by high frequency magnetic fields, as a cancer treatment method. The Czerlinski patent involves aggregation and re-suspension of fine particles in solution where the particles include magnetic material having a predetermined Curie point, and the aggregation and re-suspension is accomplished by varying the temperature above and below the Curie point.

With regard to the use of magnetic particles and chemotherapy agents in microspheres for the treatment of cancer, this technique has been successful with tumors which are localized near the surface of the human body. However, for deep seated tumors, it is not practical to provide a magnetic field which is localized deep within the body. More specifically, the magnetic field is provided by permanent magnets or electromagnets which are mounted outside of the body, and therefore provide a magnetic field which extends from the skin to the deep-seated tumor. Accordingly, if the procedure is employed in such cases, many of the carrier microspheres will be held outside of the desired cancerous zone. Further, because the magnetic field strength drops off with distance from the magnet, higher magnetic field strengths, and correspondingly higher concentrations of the chemotherapy agent will be located near the skin, outside of the deep-seated cancerous zone.

A principal object of the present invention is to overcome the limitations as outlined above on the treatment of deep-seated cancerous tumors or the like.

SUMMARY OF THE INVENTION

In accordance with the present invention, the magnetic material employed in the microsphere technique as described above, is formed of a Curie point material wherein the magnetic material loses its magnetic properties at a temperature slightly above the normal temperature of the human body; and a high frequency electric field is applied to heat up the magnetic material within the magnetic field zone but outside of the area where the tumor to be treated is located. With the magnetic particles only being magnetic in the vicinity of the tumor, the microspheres and the chemotherapy agent will be concentrated at the desired localized zone. The chemotherapy or other therapeutic agent to be associated with the microspheres may be any of the known types of chemotherapy or therapeutic substances, or may involve radioactive materials, as noted below.

In order to verify the location of the active microspheres, they may also include Technetium 99 m, or other suitable gamma ray emitting radioactive material. As a further alternative, when radiation treatment is also desired, I-131 or a comparable radioactive isotope may be used, as this iodine isotope emits both gamma rays for imaging location and beta particles for radiation treatment. Known types of gamma ray imaging equipment may be employed to determine the location and concentration of the particles, and suitable adjustments in strength and/or location of the magnetic field and high frequency electromagnetic heating arrangements, may be made to shift the concentration as needed or desired.

For the steady magnetic field, an electromagnet or several electromagnets are normally preferred for ease in adjustment, but permanent magnets may also be employed. To provide the electromagnetic radiation, waveguides with output horns may be used; high frequency coils could be employed; or dipole type radiating antenna type elements may be used, to directionally apply the radiation to the desired location. Constructive and destructive interference from more than one radiating source may be employed with cyclic phase shifting when appropriate, to heat the magnetic particles where they are not wanted, and to avoid heating the magnetic particles in the desired zone within the magnetic field where the particles are to be concentrated.

From a broad standpoint, the present invention involves the use of Curie point magnetic material, at least one magnet for providing a steady magnetic field for exerting a restraining force on the magnetic material, and the application of a high frequency electric field to selected areas within the steady magnetic field, such as close to the magnet, so that the Curie Point magnetic material may be restrained only at the desired location or locations within the magnetic field.

Other objects, features and advantages of the invention will become apparent from a consideration of the following detailed description, and from the accompanying drawings.

DETAILED DESCRIPTION

General Considerations

As mentioned above, the present invention involves the selective restraint of magnetic material having an accessible Curie point temperature, and the use of (1) a magnetic field to hold the magnetic material and (2) the use of a high frequency electromagnetic field to selectively heat the magnetic particles to a temperature above the Curie point.

In order to effect restraint of particles within a selected field zone, two conditions must be simultaneously met therein—(1) the particles must be magnetically responsive i.e., at a temperature sufficiently below the Curie point to exhibit substantial ferromagnetic exchange coupling, and (2) the static magnetic field gradient must be of adequate strength to restrain magnetically responsive particles within capillary vessels in the selected field zone.

It is necessary and sufficient that either one of these conditions be absent at sites external to the selected field zone (where it is desired to concentrate the microspheres) in order to effect free unrestrained flow of the particles.

The appropriate presence and absence of these conditions is regulated by the geometrical intersection of an oscillatory electromagnetic field and the static magnetic field, as set forth below. The effect of the oscillatory electromagnetic field is to heat up the magnetic particles and render them substantially nonmagnetic.

It is a general feature of this invention that the oscillatory electromagnetic wave intensity be absent or of negligible value in the selected target zone. Oscillatory electromagnetic waves may be locally diminished (1) by natural exponential attenuation upon passage through lossy material, and (2) cancellation of waves oppositely phased emanating from two or more sources.

SPECIFIC EXAMPLES

Figure 1:
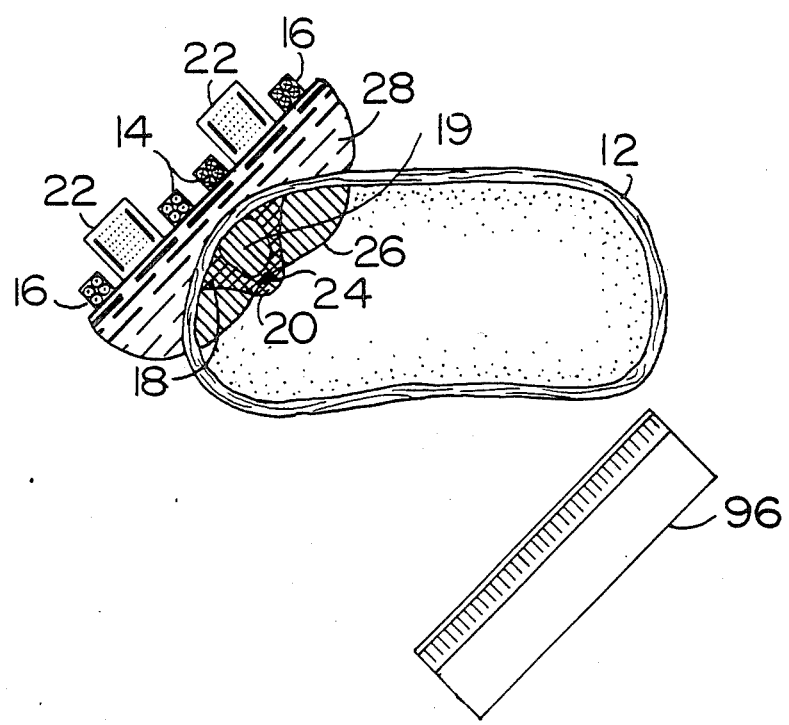
FIG. 1 shows an electromagnetic therapy system illustrating the principles of the invention.

One example illustrating the principles of the invention utilizing the former, diminution principle noted at (1) in the preceeding paragraph, is shown in FIG. 1 in cross-section.

A static magnetic field may be generated unilaterally with respect to a patient, 12, by means of a concentric coil array, including an inner coil 14 and an outer coil 16, in FIG. 1. By adjustment of the polarity and current in the individual coils 14 and 16, a region 18 of static magnetic field gradient equalling or exceeding the requisite strength is controllably projected symmetrically on the axis of the coil array 14, 16 to a desired depth. The central region 19 has a relatively low magnetic field gradient.

Figure 2:
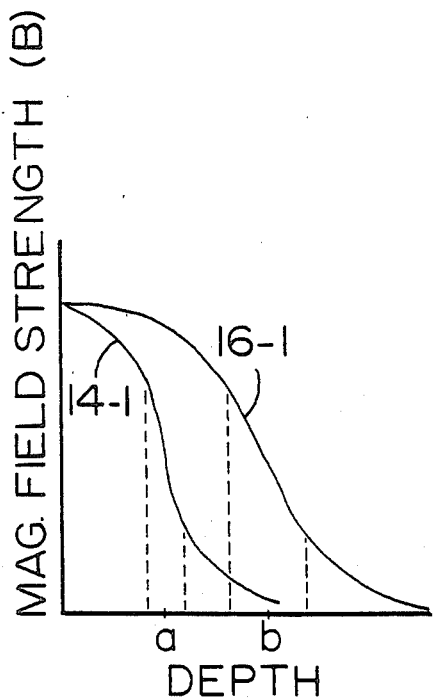
FIG. 2 is a pair of plots of magnetic field strength versus depth for two different sets of electrical currents in the electromagnets of FIG. 1.

The magnetic field strength would appear as shown in FIG. 2 along the axis of the coil array with selected energization of coils 14 and 16. The curves depict the general form of the magnetic field strength B with respect to depth in two separate examples with plot 14-1 corresponding to currents flowing principally in the inner, smaller coil 14, and plot 16-1 corresponding to substantial currents in the outer, larger coil 16. The curve characteristic of particular interest is the region of steepest slope which correlates to the maximum magnetic gradient critical to restraint. In FIG. 2, this value occurs at depth zones centered at points a and b on curves 14-1 and 16-1 respectively. The coil array is placed such that its central axis intersects the targeted zone 20 in FIG. 1, and the coil currents are adjusted until the depth of the maximum gradient coincides with zone 20.

Figure 3:
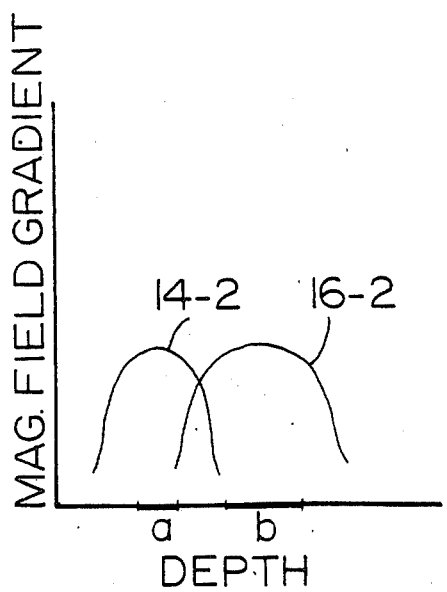
FIG. 3 shows corresponding plots of magnetic gradient versus depth for the same magnets.

The significance of the curves in FIG. 2 may be better understood when graphed as the derivative (slope) of B with respect to depth as shown in FIG. 3, with plot 14-2 relating to plot 14-1, and gradient plot 16-2 corresponding to plot 16-1. Thereby, it may be recognized that regions centered about some depth, e.g. points a and b in FIG. 3, exhibit a maximal, moderately constant, gradient.

Without an oscillatory electromagnetic field, particles would be restrained and accumulate in the entirety of region 18, FIG. 1. It is necessary however, to restrict such accumulation to a sub-region of volume 18, namely region 20 which is the targeted zone.

The confinement of particles to region 20 is accomplished in the example shown in FIG. 1 by means of an antenna array 22 directing an oscillatory electromagnetic field toward the general region of the static magnetic gradient region 18. Elements of said array are waveguide horns 22.

For example, at a frequency of 100 megahertz (MHz), human tissue attenuates the intensity by a factor of 1/e squared, or reduces the intensity to about 0.137 of its original value for every 7 cm traversed. If the closest border of the target zone were 14 cm deep, then natural attenuation would reduce the incident oscillatory wave intensity by a factor of 0.137 of 0.137 or approximately 0.02, or one-fiftieth of its original value. In order to confine the magnetic particles to the targeted zone 20, it is necessary to deliver a threshold oscillatory wave intensity I at the closet target zone border point 24 FIG. 1, 14 cm deep in this example. This value I is selected to increase the particle temperature to a marginal limit of magnetic responsiveness, or non-responsiveness.

It may be noted in this example, that the incident intensity substains an attenuation to 0.02 of its original value to ultimately deliver a threshold intensity of I at point 24. Conversely, the incident intensity must be 1/0.02 or 50 times as large as I. At depths less than that of point 24, FIG. 1, the oscillatory wave intensity, sustaining less attenuation, exceeds I, thereby heating the particles and rendering the particles magnetically non-responsive. With appropriate spatial separation and oscillatory frequency, antenna elements 22 are driven with sufficient amplitude to cause the marginal limit zone 26 to exhibit a spatial curvature, within the patient, which extends substantially beyond the limits of the restraining static magnetic field gradient, 18. Thereby, the oscillating field within the bounds 26 nullifies the magnetic responsiveness of particles throughout the high gradient region 18 except in zone 20. Because of the relatively inverted curvatures of the fields 18 and 26, zone 20 is roughly spherical in shape. At depths greater than that of point 24 FIG. 1 within zone 20, the natural attenuation reduces the oscillatory field intensity below the intensity level I, whereby the magnetically responsive particles are restrained within the targeted zone. At depths exceeding that of zone 20, the magnetic gradient falls off sufficiently so that restraint does not occur.

Thereby, in this example shown in FIG. 1, the requisite conditions are met whereby particle restraint occurs exclusively in the targeted zone 20.

Incidentally, the flexible container or bag 28 contains a dielectric fluid providing a transition for the electromagnetic waves permitting a controlled radiation pattern into the body 12 without undue reflection. The fluid within the dielectric or plastic bag 28 may be de-ionized water. This bag 28 may, for example, be of dielectric or plastic material, to avoid reflections.

Within the scope of this invention, oscillatory wave interference or cancellation may also be utilized in effecting intensity diminution at the selected target zone. One such example is depicted in cross-section in FIG. 4.

Figure 4B:
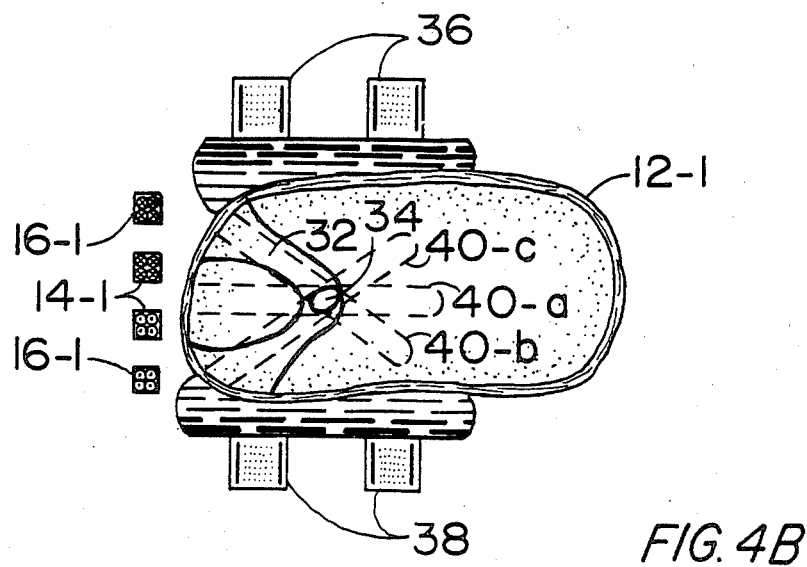
FIG. 4B shows the fields of the embodiment of FIG. 4A.
Figure 4A:
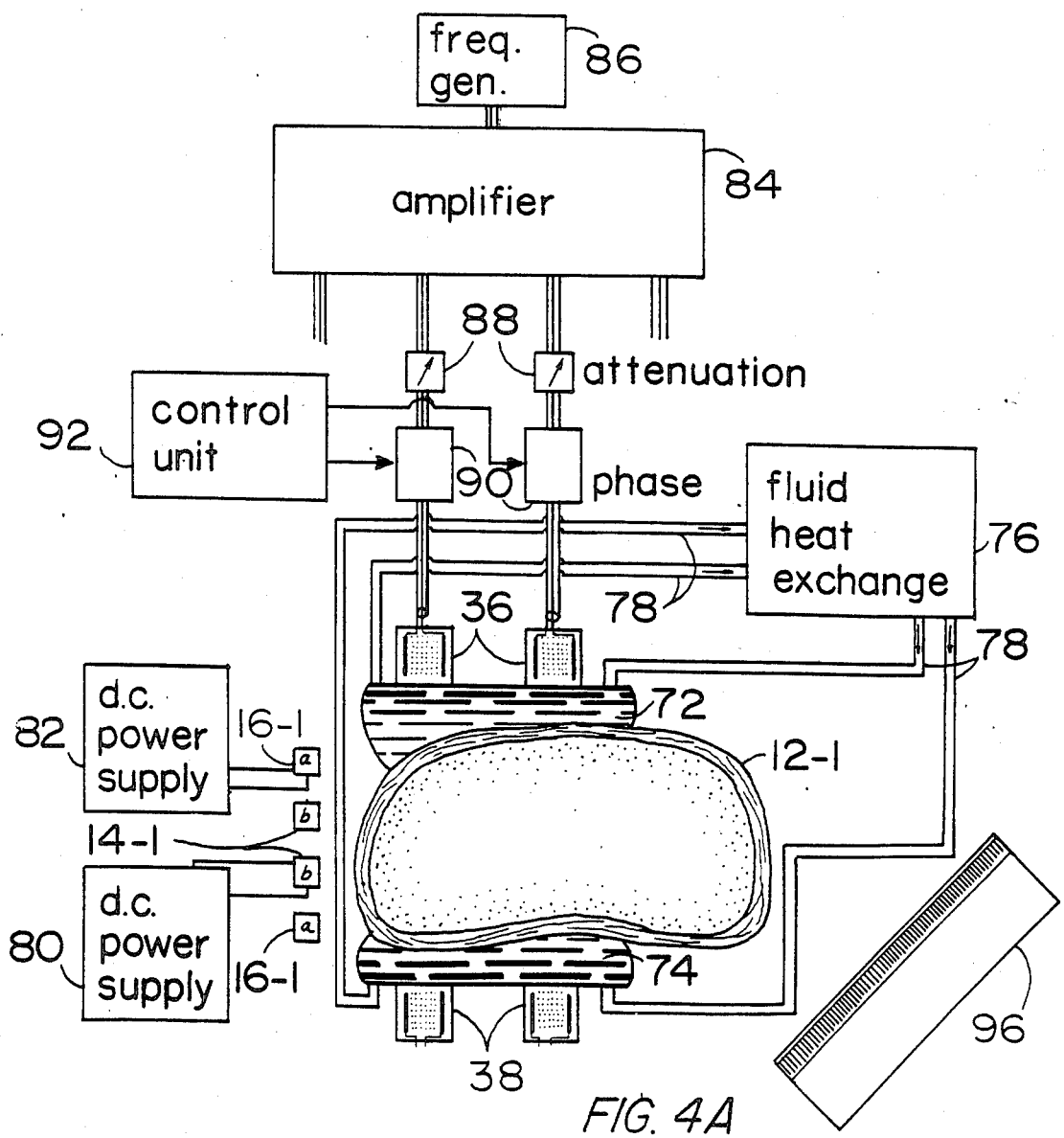
FIG. 4A is a comprehensive showing of an alternative embodiment of the invention.

The patient 12-1 is positioned next to a static magnetic field which may be generated by a coil array including coils 14-1 and 16-1 similar to that depicted in FIG. 1. A magnetic gradient region 32 in FIG. 4 is of sufficient strength to restrain magnetically responsive particles. Restraint, however, is to be restricted to a targeted zone 34 within region 32. It is then necessary to cause the particles to be rendered non-magnetic in all regions of zone 32 exclusive of the targeted zone 34.

Figure 5:
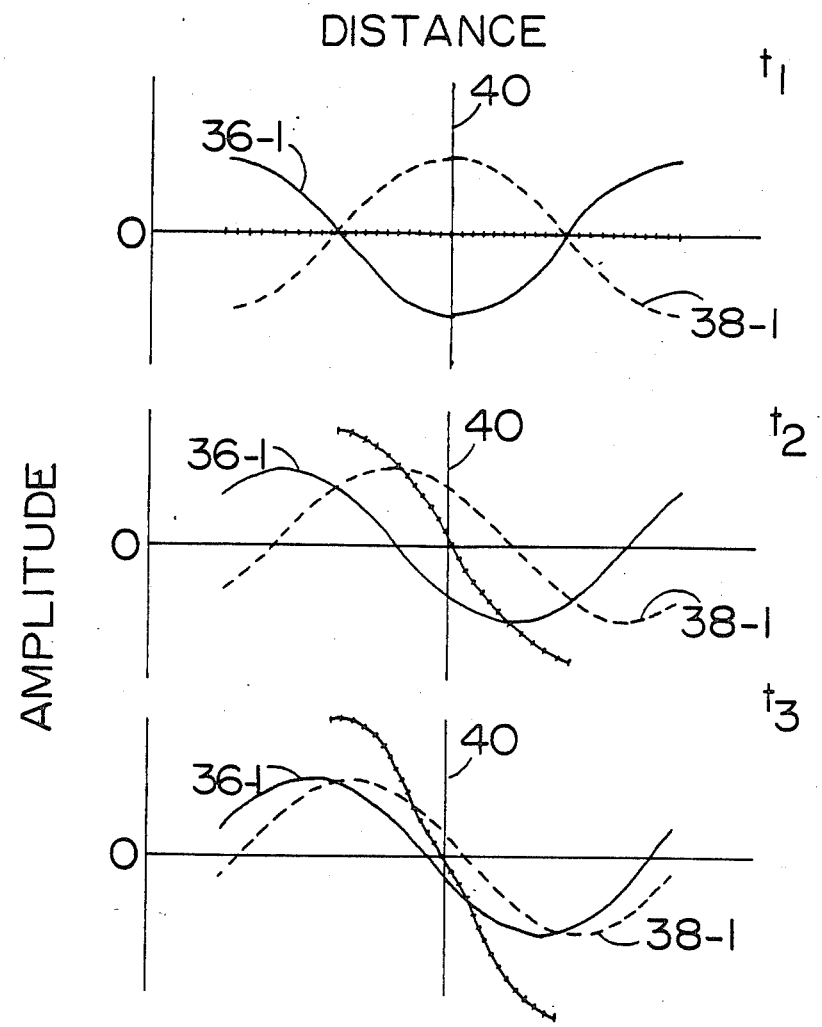
FIG. 5 is a series of plots of the interference of electromagnetic waves from two different sources such as those of FIG. 4.

Opposing planar antenna arrays 36 and 38 shown in cross-section in FIG. 4 are utilized to direct oscillatory electromagnetic radiation toward region 32. The amplitude and phase of each element in each array are controlled. If all elements within each array have the same phase, planar waves essentially parallel to the array plane are generated from each respective array. The instantaneous amplitude of such waves from arrays 36 and 38 may be described respectively as $A\sin(2\pi ft)$ and $B\sin(2\pi ft+k)$, upon arrival at the target zone plane enclosed by the dashed lines 40-a. The amplitude coefficients A and B depend upon two variables each, the attenuation sustained by the respective waves in traversing the respective distances to the target zone plane and, of course, the initial amplitude of emission from arrays 36 and 38. Accordingly, the latter variables may be adjusted to compensate for the former so that the amplitude coefficients A and B each equal a common value which we will designate as A at the target zone plane. The attenuation is dependent upon the frequency f of the waves. The relative phase of the waves in the target zone plane can be arbitrarily selected simply by retarding or advancing the phase of one of the arrays as indicated by the constant k in the following equation (1). In particular, for the amplitudes from arrays 36 and 38 to add to zero implies that:

$$A\sin(2\pi ft)+A\sin(2\pi ft+k)=0 \qquad (1)$$

for which k equal to $\pi$ (or 180 degrees) is a solution. With this relative phase condition, the waves from arrays 36 and 38 of FIG. 4, moving right and left respectively as shown in the plots of FIG. 5, totally cancel at all times at the target zone plane 40; but the intensities average to a non-zero value in the regions on either side of said plane 40 as shown in FIG. 5 for three successive instants in time, $t_1$, $t_2$ and $t_3$, in the three showings of FIG. 5. Effectively, a planar slab delineated in cross-section by lines 40-a in FIG. 4 defines a region of zero or negligible oscillatory wave intensity wherein particles remain magnetically responsive, and outside of which particles are heated by the field and rendered magnetically non-responsive.

By simultaneously retarding and advancing the individual antenna elements across the arrays 36 and 38 of FIG. 4, the aforementioned planar slab can be tilted at any desired angle. Instantaneously, the slab might be defined by plane 40-b. The rotation of this slab about an axis 42 extending centrally through arrays 36 and 38 from 40-b to 40-c and thence back to 40-b is effected by a periodic retardation and advancement of the individual antenna elements. Averaged out, only the targeted zone 34 would constantly remain in a region of sufficiently low oscillatory wave intensity for particles therein to remain unheated and magnetically responsive. All other regions of zone 32 are subjected to sufficiently substantial oscillatory wave intensity to render the particles therein magnetically non-responsive.

The foregoing examples demonstrate the principles of this invention with a circular coil array constituting a static magnetic field generator. It may be appreciated that other magnetic field generators can also be used such as a "C" shaped iron yoke magnet where the patient is placed between the magnetic poles. The magnet can be either an electromagnet or a permanent magnet.

Likewise a variety of oscillatory electromagnetic field antenna arrays and operating modes are applicable within the scope of this invention.

ENERGY ABSORPTION IN PARTICLES

A central feature of this invention is the spatially controlled disposition of oscillatory electromagnetic energy in said particles. In an idealized circumstance, such energy disposition would be zero at the targeted field zone and abruptly very high elsewhere. Specific physical interactions mediate to diminish the abruptness of the absorption transition in and out of the target field zone. However, using the techniques as described herein, together with materials having appropriate absorption characteristics and moderately abrupt Curie temperature, effective restraint in the target zone is achieved.

The absorption of oscillatory electromagnetic radiations in magnetic and in conductive matter will now be considered. For example, from the American Institute of Physics Handbook (McGraw-Hill, New York, 1957), Sec. 5 p. 90, tin and magnetic iron have very similar conductivities, being in a ratio of 1:1.2. Nevertheless, the absorption of energy flux is in a ratio of 1:16 based upon the relative penetration depths at which the flux has diminished to $1/e$ squared for radiation in the range of 1 to 3000 MHz. This rather marked absorption difference is attributed to the relative magnetic permeabilities which are in a ratio of 1:200. Electromagnetic radiation, which consists of oscillatory electric E and magnetic B vector components, is absorbed in relation to electric conductivity and magnetic permeability, respectively. Accordingly, it may be understood that tin and magnetic iron both absorb a certain similar proportion of the electric component but the magnetic iron additionally absorbs a very large proportion of the magnetic component. If both components are radiated at equal amplitudes, it may be expected that magnetically responsive substances will absorb energy predominantly from the magnetic component.

The relevance of this interaction to the present invention may now be understood. The particles of this invention have a magnetic permeability which is very sensitively temperature dependent. In the targeted field zone, the particles are to be maximally magnetically responsive in order to effect restraint with respect to the static magnetic field. In regions immediately exterior to this zone, the particles are to be minimally magnetically responsive in order to allow unrestrained flow into the zone.

If, for example, the electromagnetic radiation immediately exterior to the zone were ten times as high as in the zone, then the particles would be expected to sustain a ten-fold higher energy absorption and a concurrent temperature rise outside the zone. However, since the particles are deliberately designed to exhibit a substantial reduction in magnetic permeability in response to a substantial temperature rise, the absorption of the magnetic component of oscillatory electromagnetic energy is severely diminished. If the magnetic component is the predominant source of energy, then the desired effect partially cancels the means to achieve that effect. That is, an initially high temperature rise brought about by a strong absorption of the magnetic component is quickly followed in equilibrium by a partial loss in temperature as the magnetic component is less strongly absorbed. Since the final equilibrium temperature is not as high as the brief initial temperature, the particles immediately exterior to the zone sustain only a partially reduced magnetic responsiveness and may exhibit a degree of undesired restraint in response to the static magnetic field. Effectively, the minimum size of the targeted field zone is increased somewhat and the concentration of restrained particles is not as abruptly delineated by the zone.

As developed below, however, the multiplicity of antenna elements may be so configured and phased so as to substantially cancel the oscillatory magnetic components and augment the oscillatory electric components in the aforementioned regions exterior to the targeted field zone. Since the interaction of the particles with regard to the oscillatory electric component is effectively independent of temperature, the energy absorption of the electric-enhanced oscillatory field is essentially proportional to the intensity of the field.

This type of arrangement increases the sharp delineation of the particle restraint zone.

Figure 6:
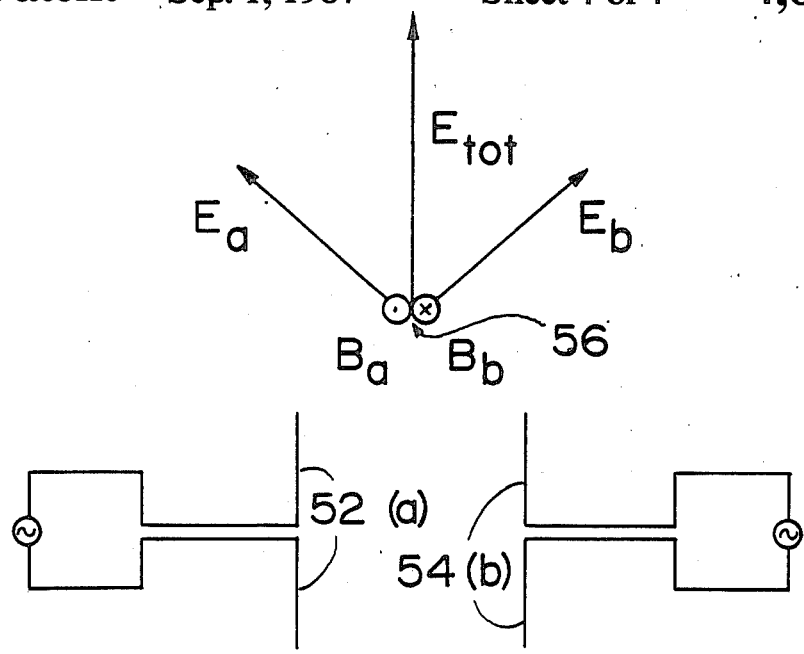
FIG. 6 is a diagrammatic showing of electromagnetic wave interaction.
Figure 7:
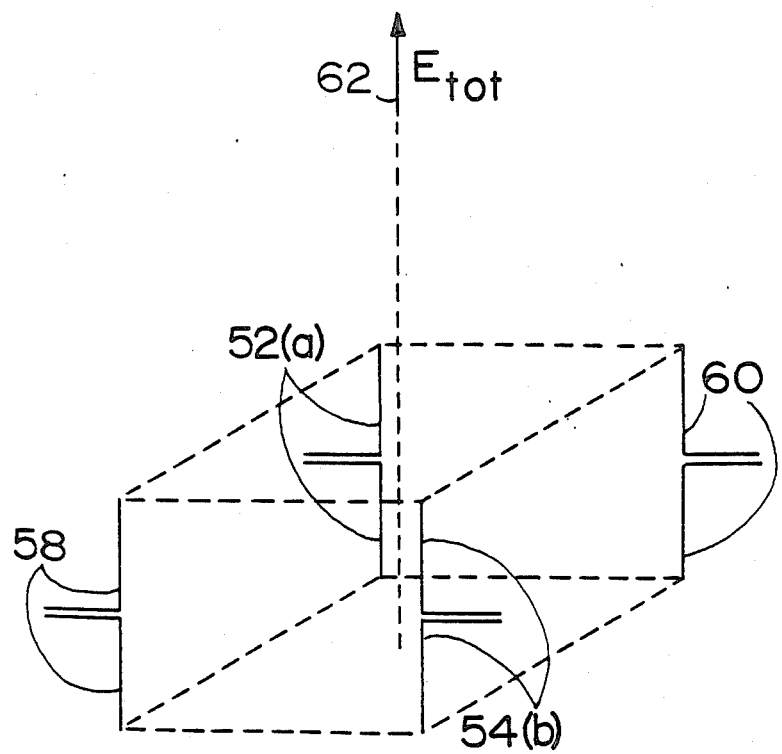
FIG. 7 is another diagrammatic showing of electromagnetic wave combination from four dipoles.

Specifically, consider FIG. 6 where the instantaneous oscillatory field components are generated from a pair of equally driven antenna dipole elements 52(a) and 54(b). The respective resultant magnetic components $B_a$ and $B_b$ at the point 56 are oppositely oriented, perpendicular to the plane of the page, thereby cancelling. The electric components add vectorially giving a value $E_{tot}$ significantly larger than the components themselves. Extending this configuration to a second pair of antenna elements 58 and 60, where all four elements are on the vertical edges of a box-like geometrical shape of square cross section, as shown in FIG. 7, allows the generation of a strong electric oscillatory field located centrally above as indicated at reference numeral 62. The corresponding net magnetic component remains at a constant zero magnitude.

It will be appreciated from the mutually perpendicular orientations of the electric and magnetic components for any oscillatory field source, that a variety of antenna element types may be operated conjunctively so as to nullify the net magnetic components within a region. Accordingly, this invention is not restricted to the illustrated configurations which are presented as examples.

PARTICLE PROPERTIES

Figure 8:
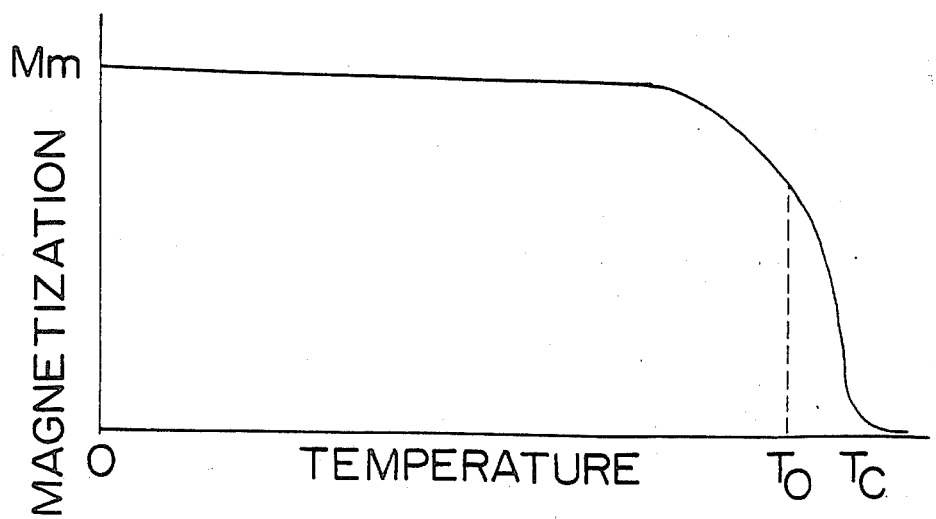
FIG. 8 is a plot of magnetization versus temperature, for Curie point materials.

A number of substances called ferromagnetics, such as iron, may be very strongly magnetized while in the presence of a magnetic field. Most of these substances exhibit magnetization versus temperature curves similar in shape to FIG. 8 but differing in scale. For example, the magnitude of the maximum magnetization $M_m$ and the temperature $T_c$ on the absolute scale varies considerably among the known ferromagnetics. The value $T_c$ is the temperature at which the extrapolated curve intersects the axis, and is known as the Curie point. A substance responding as in FIG. 8 is said to be ferromagnetic when below the Curie point, $T_c$. At temperatures above the Curie point $T_c$, the curve descent levels off somewhat wherein a substance is said to be paramagnetic.

The very large magnetization exhibited by ferromagnetic substances is a collective quantum mechanical phenomenon known as exchange coupling. When aggregates of certain atomic species are formed, a very large percentage of the individual atomic magnetic moments align together. The broad gradually sloping region of FIG. 8 below $T_c$ shown in FIG. 8, indicates nearly 100% alignment. As temperature increases up to $T_c$, this exchange coupling is disrupted by thermal agitation with a concurrent decrease in magnetization. The paramagnetic state, above $T_c$, is said to exist when sufficient disruption occurs such that the coupling is totally broken and the atoms act independently in their alignment response. The maximum magnetization $M_m$ for the purposes of this invention, should be substantial, ideally comparable to iron and other strong ferromagnetics. The particles of this invention should also exhibit response wherein human body temperature, which is 310 degrees K., or 98.6 degrees Fahrenheit, should fall at a point $T_O$ on the shoulder of the curve at the onset of rapid descent as in FIG. 8. For a value of $T_O$ so situated, $T_c$ is typically a modest increment higher on the order of magnitude of 10 degrees Kelvin. While it is not necessary that the induced temperature increase actually reach or exceed $T_c$, it is essential that a very large relative decrease in magnetization be effected. Nevertheless, substances having Curie points slightly above 310 degrees K. are indicative of good candidates for the particles.

Pure iron for example is inappropriate, having a Curie temperature of 1040 degrees K. Several possible choices and their Curie temperature in degrees Kelvin include, CrTe, 320; $Cr_3Te_4$, 325; $Nd_2Fe_7$, 327; Ni-Cr (5.6% atomic % Cr), 324; and Fe-Ni (about 30% Ni) 340 as well as many other combinations. Furthermore, it is known in the art that small percentage variations in composition can increase or decrease the Curie temperature by several degrees. For instance, the Fe-Ni alloy can be altered to provide a lower Curie temperature of perhaps 320.

The Fe-Ni alloy is also desirable since it is a moderately good conductor, essential to absorption of the oscillatory electric component. Fe-Ni also exhibits magnetization comparable to that of pure iron, Fe. Biologically, the elements Fe and Ni do not exhibit the undesirable toxicity common to an element such as chromium, Cr, included in some of the afore-mentioned combinations, and the material is therefore substantially medically inert.

ENERGY ABSORPTION AND TEMPERATURE RISE

The purpose of the oscillatory wave generator is to significantly raise the particle temperature in regions exterior to the targeted zone. The temperature rise is caused by the preferential conversion of electromagnetic energy to thermal energy by the particles. Conversely, the temperature of surrounding tissue is not significantly raised when subjected to the same oscillatory waves.

The underlying physical principles are readily understood in conjunction with the relative absorptivity of good conductors and patient tissue. For example, at 100 MHz, the intensity decreases by a factor 1/e squared in 0.0007 cm of copper and in 7 cm of tissue, indicating that a good conductor such as copper is 10,000 times as absorptive as tissue.

The thermal energy of the particles is subsequently dissipated to surrounding tissue. However, the total mass of injected particles is many orders of magnitude less than that of the patient. Consequently, the patient is effectively an infinite heat sink negligibly increased in temperature by the relatively small total heat content transferred from the particles.

Thereby, the particles are readily increased in temperature whereas direct and indirect energy transfer to tissue is negligible resulting in an insignificant rise in overall patient temperature.

IMPLEMENTATION OF APPARATUS

The oscillatory electromagnetic field may be provided by devices such as a MA-150 waveguide antenna horn coupled to a BSD-1000 RF power generator, both manufactured by BSD Medical Corporation, Salt Lake City, Ut.

These devices are conventionally used to achieve regional hyperthermia by selectively directing radio frequency (RF) electromagnetic waves of high intensity at a tumor site within a patient. Certain tumor types are temperature sensitive compared to normal tissue. In this regard, a temperature increase of about 5 degrees K. sustained for approximately 20 minutes is often effective in killing tumor cells, while normal cells are left undamaged.

A coaxial conductor cable interconnects the BSD-1000 to a termination within the MA-150 waveguide antenna horn consisting of plate electrodes across a dielectric layer.

The antenna horn facilitiates directivity of the projected electromagnet waves. A flexible water bag affixed to the mouth of the antenna horn is pressed against the patient over the site targeted for the application of electromagnetic energy. The water efficiently couples the RF waves into tissue and minimizes reflections. Thermal energy generated in the water is continuously removed by pumping through an ice-filled heat exchanger. By this means, the surface of the patient is cooled through a thermal conductive process which allows for additional control of temperature within the patient.

The BSD-1000 RF power generator provides fully adjustable power from 5 watts to 250 watts over the frequency range of 95 MHz to 1000 MHz. Although heating may be obtained over a wider range, for the purposes of the present invention, a frequency range of about 50 megahertz or 50,000,000 cycles per second, up to about 200 megahertz is preferred. The reason that this range is preferred is that above 50 megahertz, there is more absorption by the particles and less by the human body; and above 200 megahertz, hot spots may develop near the horns. However, effective heating may be accomplished over a much broader range of frequencies.

More than one MA-150 antenna horn may be driven by the BSD-1000 using power splitters. The MA-150 units may be arranged in an array such that each unit represents an antenna element of this invention. The power output from the BSD-1000 to each MA-150 unit may be phase shifted and attenuated to control of the oscillatory wave intensity as described with respect to this invention.

E-field sensors available from BSD are placed in skin contact on the patient to monitor the incident electric field and estimate the resultant internal temperature distribution.

The MA-150 horns project electromagnetic waves with the electric and magnetic vectors mutually perpendicular to each other and also to the direction of the wavefront propagation as is common to all such electromagnetic propagation. Thereby, as described hereinabove, two adjacent MA-150 horn units may be placed to produce total cancellation of the magnetic vector and augment the electric vector in the neighborhood of a mid-plane between the units. Correspondingly, opposing MA-150 units produce an intermediate null plane by destructive interference, as described herein, using opposite relative phase.

The component devices used in hyperthermia are necessarily operated at high power levels to produce gross regional temperature increases of about 5 degrees K. in and around targeted tissue.

For the purposes of this invention, sub-therapeutic power levels with respect to hyperthermia, are used such that actual regional tissue temperature at all sites is never increased by more than 2 degrees K., and generally by less than 1 degree K. Nevertheless, when such tissue contains particles as described herein, then said particles locally sustain a substantially higher temperature increase of approximately 10 degrees K. as demonstrated by loss of magnetic responsiveness.

Furthermore, the objective of hyperthermia is, ideally, a focal heating of targeted tissue e.g., a tumor. This focal heating may be augmented by constructive interference of horn antennae at the depth of the tumor whereas in the context of the present invention, a significantly reduced RF intensity exists at the targeted tissue. It may be appreciated that attenuation by tissue absorption, and by phase inversion of the electric vectors from opposing horn antennae and destructive interference, or cancellation, may be used to produce this reduced RF intensity.

The static magnetic field may be produced by Model HS-1785-4A DC power supplies combined with circular coil elements such as those in the Model M-4074 assembly, both available from Walker Scientific Inc., Rockdale Street, Worcester, Mass. 01606. The power supply generates 0–85 amps at 0–170VDC. The coil elements are wound with aluminum foil 6 inches wide with plastic film insulation between the turns. Each wound coil is affixed to a flat aluminum plate by epoxy resin and water channels milled into the plate facilitate cooling of the coil during operation.

A concentric pair of such coils with diameters of twenty inches and eight inches provides an effective depth controllable gradient with magnetic strength in excess of 1000 gauss. Each coil is driven by a separate power supply so that current and polarity is individually controllable.

The magnetic field may be mapped with a gaussmeter such as the Model MG-3D Hall effect unit available from Walker Scientific, Inc. This instrument can measure fields in the range of 10 to 100,000 gauss with an accuracy of ±0.1%.

PARTICLE PREPARATION

A large variety of appropriate metallic alloys in powder form are available from manufacturers such as Ashland Chemical Co., P.O. Box 2219, Columbus, OH 43216. A comprehensive reference text prepared by R. M. Bozorth lists several hundred alloys and their respective Curie temperatures.

Bozorth's references indicate that an alloy such as 70% Fe, 30% Ni has an appropriate Curie temperature. However, the Curie temperature exhibits a very strong compositional sensitivity, increasing several tens of degrees for each additional percent of Ni. Accordingly, commercially supplied powder consisting of approximately 100 Angstrom size particles exhibits a wide dispersion of Curie temperatures. Particles in an appropriate Curie temperature range such as 320±5 degrees K. may be separated from the particles of inappropriate Curie temperature, by the following steps.

The particles are first coated with a fluorocarbon suspension agent available from Ferrofluidics Corporation of Burlington, Mass. The resultant ferrofluid is then heated in a water bath to 340 degrees K. A permanent magnet is used to extract those particles from the ferrofluid which are still magnetically responsive. This process is repeated at 5 degree K. cooling increments down to 315 degrees K. Thereby, the singular extraction at 315 degrees K. exhibits the appropriate Curie transition temperature and is retained, the other extractions being discarded.

Senyei and Widder in U.S. Pat. No. 4,247,406 have suggested the use of human serum albumin (HSA) microspheres as carriers of magnetically responsive particles and therapeutic substances such as chemotherapy agents, since HSA is not readily extracted from the blood by the body's defense systems. Thereby, sufficient time is allowed for an externally applied static magnetic field to trap a substantial quantity of such HSA microspheres flowing in the bloodstream. Microspheres for this invention are prepared as described by Widder and Senyei in U.S. Pat. No. 4,247,406 Example I, page 7 except that in place of $Fe_3O_4$, particles, Fe-Ni alloy particles of 320 degrees K. Curie temperature are used.

In addition, Tc-99 m is used in place of the I-125 indicated by Widder and Senyei.

In the context of the present invention, a focal concentration of particles is achieved by the conjunctive action of static magnetic fields and oscillatory fields controlling the magnetic responsiveness of said particles. As an additional feature of this invention, radioactive gamma ray emitting atoms may be combined with the particles to provide feedback means of assessing the locus of focal concentration.

Technetium 99 m, Tc-99 m, is a suitable gamma emitting radioactive atom for this application whereas I-125 is not. Medi-Physics Inc., 5801 Christie Avenue, Emeryville, CA 94608 is one of several manufacturers supplying Tc-99 m for medical imaging procedures. Medi-Physics also provides HSA in a suitable form for incorporation of Tc-99 m.

Alternatively, I-131 may be used when imaging as well as radiation therapy is the objective. I-131 emits gamma rays for the former and beta particles for the latter.

A gamma ray imaging camera such as the Data Mo (manufactured by Picker International, Inc., 12 Clintonville Road, P.O. Box 99, Northford, CT 06472) may be used to ascertain the spatial coordinates and concentration of gamma ray emitting radioactive atoms attached to the magnetically responsive particles. The camera head in this application must be magnetically shielded to allow it to operate properly in the presence of the static magnetic field. An enclosure of Permalloy 80 sheet metal, 0.06 inches thick, available from Magnetics Specialty Metals Division, Butler, PA 10661 may be used to provide the requisite magnetic shielding. The data from the camera may be used to adjust the static magnetic and the oscillatory fields to target the concentration point of the HSA microspheres.

By way of completeness, certain of the components of FIG. 4 not mentioned in detail hereinabove, include the water bags 72 and 74 containing deionized water to facilitate coupling of electromagnetic waves from horns 36 and 38 into the body. The fluid heat exchanger 76 is coupled to the water bags 72 and 74 by flexible tubes 78 to maintain normal surface body temperature. The coils 14-1 and 16-1 are energized by the adjustable power supplies 80 and 82, respectively. High frequency electromagnetic energy is supplied to horns 36 and 38 from the amplifier 84, coupled to the frequency generator 86. The amplitude of the applied electromagnetic waves may be controlled by the attenuators 88, and the phase by the phase shifters 90, as controlled by the control unit 92. A duplicate set of energization and control circuitry is provided for horns 38 and the two energization and control circuits are synchronized to provide the desired relative phase shift as discussed above. Also shown in FIG. 4 is the gamma ray camera imaging head 96, of the type mentioned above, and provided with suitable magnetic shielding.

In conclusion, it is to be understood that the foregoing detailed description relates to preferred embodiments illustrating the principles of the invention. Other arrangements for applying electromagnetic energy for heating the magnetic particles, and for providing a magnetic field gradient may be used. Other types of medically inert Curie point materials having the proper transition temperature may also be employed. It is to be understood, therefore, that the present invention is not limited specifically to the precise showings of the drawings and the specific matters set forth in the detailed description.

What is claimed is:

1. A method for applying a therapeutic agent to a treatment zone in a patient, which treatment zone is not adjacent the skin of the patient, comprising:

applying a steady or low frequency magnetic field to the patient to include the treatment zone;

supplying microspheres for circulation through the patient to include said zone, said microspheres including a therapeutic agent, and also includes medically bodily compatible magnetic material having a Curie point at which the magnetic material becomes substantially non-magnetic slightly above the normal body temperature of the patient; and applying high frequency electromagnetic field energy to said patient where said magnetic field is applied to said patient, except to said treatment zone, to heat up said magnetic material to demagnetize it so the microspheres are not restrained by said magnetic field except in said treatment zone.

2. A method as defined in claim 1 including the step of adding a radiation emitting material to said microspheres and determining the concentration of said microspheres at different locations within said patient from the output radiation.

3. A method as defined in claim 2 including the additional step of modifying the application of the magnetic field and the high frequency electromagnetic field to increase the concentration of microspheres in the treatment area in accordance with the concentration determination.

4. A method as defined in claim 1 wherein the application of a high frequency field includes the step of directing high frequency electromagnetic field energy having the same frequency from two different radiating sources, and means for adjusting the relative phase of the radiation for destructive interference or substantial cancellation at the treatment zone.

5. A method as defined in claim 1 wherein the magnetic field is applied to the patient from a predetermined direction adjacent the skin of the patient and wherein said high frequency electromagnetic energy is applied to the patient from substantially the same direction, at an intensity level sufficient to heat the magnetic material toward the adjacent surface of the body but not to heat the magnetic material in the treatment area beyond the Curie point temperature.

6. A method as defined in claim 1 wherein the applying of a high frequency electromagnetic field provides a sharper delineation of microsphere concentration at the boundaries of the treatment zone by the cancellation of magnetic field components adjacent to said treatment zone n conjunction with the magnetic materials having an electrically conductive composition.

7. A system as defined in claim 6 wherein said objects including Curie point material are microspheres which also contain a therapeutic agent.

8. A system for applying a therapeutic agent to a treatment zone in a patient, which treatment zone is not adjacent the skin of the patient, comprising:
means for applying a steady or low frequency magnetic field to the patient to include the treatment zone;
means for supplying microspheres for circulation through the patient to include said zone, said microspheres including a therapeutic agent, and also includes medically, bodily compatible magnetic material having a Curie point at which the magnetic material becomes substantially non-magnetic slightly above the normal body temperature of the patient; and
means for applying high frequency electromagnetic field energy to said patient where said magnetic field is applied to said patient, except to said treatment zone, to heat up said magnetic material to demagnetize it so the microspheres are not restrained by said magnetic field except in said treatment zone.

9. A system as defined in claim 8 wherein radiation emitting material is included in said microspheres.

10. A system as defined in claim 9 including means sensitive to said radiation for determining the location of said microspheres.

11. A system as defined in claim 8 wherein means for emitting gamma rays and means for emitting beta rays are included in said microspheres.

12. A system as defined in claim 8 wherein the means for applying a high frequency field includes means for directing high frequency electromagnetic field energy having the same frequency from two different radiating sources, and means for adjusting the relative phase of the radiation for destructive interference or substantial cancellation at the treatment zone.

13. A system as defined in claim 8 wherein the magnetic field is applied to the patient from a predetermined direction adjacent the skin of the patient and wherein said high frequency electromagnetic energy is applied to the patient from substantially the same direction, at an intensity level sufficient to heat the magnetic material toward the adjacent surface of the body but at an intensity insufficient to heat the magnetic material in the treatment area beyond the Curie point temperature.

* * * * *